United States Patent
Chheda et al.

(10) Patent No.: US 10,253,009 B2
(45) Date of Patent: Apr. 9, 2019

(54) ONE-STEP PRODUCTION OF FURFURAL FROM BIOMASS

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/502,870

(22) PCT Filed: Aug. 13, 2015

(86) PCT No.: PCT/US2015/044983
§ 371 (c)(1),
(2) Date: Feb. 9, 2017

(87) PCT Pub. No.: WO2016/025674
PCT Pub. Date: Feb. 18, 2016

(65) Prior Publication Data
US 2017/0233362 A1 Aug. 17, 2017

Related U.S. Application Data

(60) Provisional application No. 62/037,200, filed on Aug. 14, 2014.

(51) Int. Cl.
C07D 307/48 (2006.01)
C07D 307/50 (2006.01)
C13K 13/00 (2006.01)

(52) U.S. Cl.
CPC ......... C07D 307/50 (2013.01); C07D 307/48 (2013.01); C13K 13/002 (2013.01)

(58) Field of Classification Search
CPC ... C07D 307/50; C07D 307/48; C13K 13/002
See application file for complete search history.

(56) References Cited

U.S. PATENT DOCUMENTS

| | | | |
|---|---|---|---|
| 2,078,241 A | 4/1937 | Fulmer et al. | |
| 2,536,732 A | 1/1951 | Dunlop | |
| 4,409,032 A | 10/1983 | Paszner et al. | |
| 4,461,648 A | 7/1984 | Foody | |
| 4,533,743 A | 6/1985 | Medeiros et al. | |
| 5,820,687 A | 10/1998 | Farone et al. | |
| 8,168,807 B2 | 5/2012 | Wabnitz et al. | |
| 8,466,242 B2 | 6/2013 | Geremia et al. | |
| 2010/0019191 A1 | 1/2010 | Hoffer et al. | |
| 2010/0122152 A1 | 5/2010 | Chamberlain et al. | |
| 2010/0312028 A1 | 12/2010 | Olson et al. | |
| 2012/0107887 A1 | 5/2012 | Chheda et al. | |
| 2012/0157697 A1 | 6/2012 | Burket et al. | |
| 2012/0302765 A1 | 11/2012 | Dumesic et al. | |
| 2013/0168227 A1* | 7/2013 | Fagan | C07D 307/48 203/35 |
| 2013/0295629 A1 | 11/2013 | Weider et al. | |
| 2014/0018555 A1 | 1/2014 | DeVries et al. | |
| 2014/0107355 A1 | 4/2014 | Dumesic et al. | |

FOREIGN PATENT DOCUMENTS

WO 2007009463 1/2007

OTHER PUBLICATIONS

Lange, J-P., "Furfural—a promising platform for lignocellulosic biofuels." ChemSusChem 5.1 (2012): 150-166.*
Viell, J., "Is biomass fractionation by Organosolv-like processes economically viable? A conceptual design study." Bioresource technology 150 (2013): 89-97.*
Galbe, et al.; "A review of the production of ethanol from softwood"; Appl. Microbiol. Biotechnol.; vol. 59; pp. 618-628; 2002.
Möller; "Outputs from the EPOBIO project"; published by CPL Press, Tall Gables, The Sydings Speen, Newbury, Berks RG14 TRZ UK; 2006.
Ong; "Conversion of Lignocellulosic Biomass to Fuel Ethanol—A Brief Review"; The Planter; vol. 80, No. 941; pp. 517-524; 2004.
Mosier, et al.; "Features of promising technologies for pretreatment of lignocellulosic biomass"; Bioresource Technology; vol. 96; pp. 673-686; 2005.
Holtzapple, et al.; The Ammonia Freeze Explosion (AFEX) Process; Applied Biochemistry and Biotechnology; vol. 28/29; pp. 59-74; 1991.
Kumar, et al.; "Methods for Pretreatment of Lignocellulosic Biomass for Efficient Hydrolysis and Biofuel Production"; Ind. Eng. Chem. Res.; vol. 48; pp. 3713-3729; 2009.
Lavarack, et al.; "The acid hydrolysis of sugarcane bagasse hemicellulose to produce xylose, arabinose, glucose and other products"; Biomass and Bioenergy; vol. 23; pp. 367-380; 2002.
Yang et al.; One-Step Catalytic Transformation of Carbohydrates and Cellulosic Biomass to 2,5 Dimethyltetrahydrofuran for Liquid Fuels; ChemSusChem; vol. 3; pp. 597-603; 2010.

* cited by examiner

Primary Examiner — John M Mauro

(57) ABSTRACT

Methods and processes for the production of valuable organic products and alcohols from biomass using a single-step dehydration extraction process having numerous advantages over prior production methods are described.

15 Claims, 3 Drawing Sheets

US 10,253,009 B2

ONE-STEP PRODUCTION OF FURFURAL FROM BIOMASS

PRIORITY CLAIM

The present application is the National Stage (§ 371) of International Application No. PCT/US2015/044983, filed Aug. 13, 2015, which claims priority from U.S. Patent Application No. 62/037,200, filed Aug. 14, 2014 incorporated herein by reference.

FIELD OF THE INVENTION

The inventions disclosed and taught herein relate generally to processes for treating biomass, and more specifically to the treatment of biomass feedstocks for the production of furfural and similar organic intermediates.

BACKGROUND OF THE INVENTION

Description of the Related Art

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. A number of approaches to overcome this recalcitrance have been performed and the breakdown of these polymers into sugars, saccharification, has a long history. General methods are outlined schematically in FIG. 1.

The original approaches dating back to the early 19th century involve complete chemical hydrolysis using concentrated mineral acids such as hydrochloric acid, nitric, or sulfuric acid. Numerous improvements to these processes have been made earning higher sugar yields from the biomass feedstock. These higher acid concentration approaches provide higher yields of sugars, but due to economic and environmental reasons the acids must be recovered. The primary obstacle to practicing this form of saccharification has been the challenges associated with recovery of the acid [M. Galbe and G. Zacchi, *Appl. Microbiol. Biotechnol.* Vol. 59, pp. 618-628 (2002)]. Recent efforts toward separating sulfuric acid and sugars using ion resin separation or hydrochloric acid and sugars via an amine extraction process and subsequent thermal regeneration of the acid have been described in U.S. Pat. No. 5,820,687. However, both of these approaches are cumbersome and expensive in practice.

Dilute acid processes have also been attempted to perform chemical saccharification and one such example is the Scholler-Tornesch Process. However, usage of dilute acid requires higher temperatures and this usually results in low yields of the desired sugars due to thermal degradation of the monsaccharides. Numerous approaches of this type have been made in the past and all have failed to meet economic hurdles. See Lim Koon Ong, Conversion of lignocellulosic biomass to fuel ethanol—A brief review, The Planter, Vol. 80, No. 941, August 2004 and Cell Wall Saccharification, Ralf Moller, Outputs from the EPOBIO project, 2006; Published by CPL Press, Tall Gables, The Sydings, Speen, Newbury, Berks RG14 1RZ, UK.

The saccharification of the cellulose enzymatically holds promise of greater yields of sugars under milder conditions and is therefore considered by many to be more economically attractive. The recalcitrance of the raw biomass to enzymatic hydrolysis necessitates a pretreatment to enhance the susceptibility of the cellulose to hydrolytic enzymes. A number of pretreatment methods, such as described by Mosier, et al. [*Bioresource Technology*, Vol. 96, pp. 673-686 (2005)], have been developed to alter the structural and chemical composition of biomass to improve enzymatic conversion. Such methods include treatment with a dilute acid steam explosion, as described in U.S. Pat. No. 4,461,648, hydrothermal pretreatment without the addition of chemicals as described in WO 2007/009463 A2, ammonia freeze explosion process as described by Holtzapple, M. T., et al. [*Applied Biochemistry and Biotechnology*, 28/29, pp. 59-74], and an organosolve extraction process described in U.S. Pat. No. 4,409,032. Despite these approaches, such pretreatment has been cited as the most expensive process in biomass-to-fuels conversion [*Ind. Eng. Chem. Res.*, Vol. 48(8), 3713-3729, (2009)].

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that enzymatic Saccharification is successful. The parameters, which can be employed to control the conditions of the pretreatment, are time, temperature, and acid loading. These are often combined in a mathematical equation termed the combined severity factor. In general, the higher the acid loading employed, the lower the temperature that can be employed; this comes at a cost of acid and its recycle. Conversely, the lower the temperature, the longer the pretreatment process takes; this comes at the cost of volumetric productivity. It is desirable to lower the temperature because pentose sugars readily decompose to form furfurals and other species, which represents a yield loss, and these compounds are poisons to downstream fermentation. However, the use of the higher concentrations of acid required to lower the pretreatment temperatures below that where furfural formation becomes facile [B. P. Lavarack, et al., *Biomass and Bioenergy*, Vol. 23, pp. 367-380(2002)] once again requires the recovery of the strong acid. If dilute acid streams and higher temperatures are employed the pretreatment reaction produces increased amounts of furfural and the acid passing downstream must be neutralized resulting in inorganic salts which complicates downstream processing and requires more expensive waste water treatment systems.

In US2012/157697, a process for preparing furfural is described wherein a biomass feedstock is mixed with water and an acid and the obtained mixture is subsequently combined with an organic solvent. A disadvantage of the process of US2012/157697 is that significant amounts of water and organic solvent are lost during the process. In addition, the process of US2012/157697 uses a very high excess of organic solvent compared to water, i.e. an organic solvent to water ratio of 15:1. This further increases solvent losses, while at the same time requires the provision of a large solvent inventory.

The inventions disclosed and taught herein are directed to methods for the synthesis of furfural and similar organic materials from a biomass feedstock using a system that allows for the single step extraction of $C_5$-containng products and the dehydration of such products, as well as the organic streams from the process steps to be readily recovered or recycled into the production system.

BRIEF SUMMARY OF THE INVENTION

The objects described above and other advantages and features of the invention are incorporated in the application as set forth herein, and the associated appendices and drawings, related to systems and methods for the synthesis of furfural and other organic intermediate compounds from a biomass feedstock using one-step $C_5$-product extraction and dehydration process.

Accordingly, the invention provides a process for converting biomass into furfural, the process comprising the steps of:
  (a) providing a pentosan-containing biomass material;
  (b) subjecting the pentosan-containing biomass material to an acid catalyzed digestion process and a dehydration reaction in a digestion vessel at a temperature greater than about 100° C. in the presence of an acid, water and a water-immiscible organic solvent to produce a digested product stream comprising water, organic solvent, furfural and solids;
  (c) separating the digested product stream into a liquid product stream and a solids product stream, the liquid product stream comprising water, organic solvent and furfural;
  (d) subjecting the liquid product stream to a liquid-liquid extraction for a period of time sufficient to separate the liquid product stream into an aqueous stream and an organic product stream, the organic product stream comprising furfural;
  (e) separating furfural from the organic product stream to yield furfural and organic solvent; and
  (f) treating the solids product stream to further remove organic solvent to yield an organic solvent-depleted solids product stream and organic solvent.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
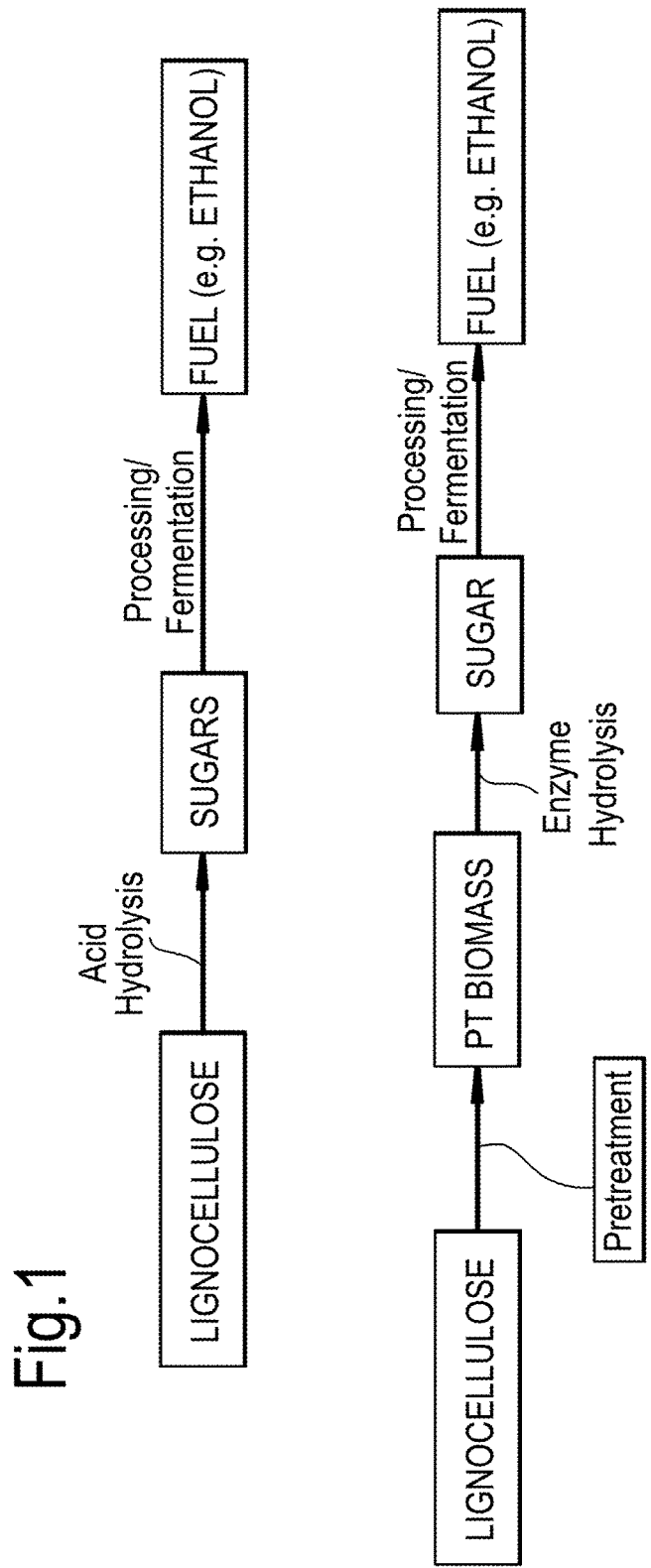
FIG. 1 illustrates a block flow diagram of lignocellulose treatment methods.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DEFINITIONS

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further in this connection, certain features of the invention, which are, for clarity, described herein in the context of separate embodiments, may also be provided in combination in a single embodiment. Conversely, various features of the invention that are, for brevity, described in the context of a single embodiment, may also be provided separately or in any sub-combination.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "contacting", as used herein, refers to the process of bringing into contact at least two distinct species such that they can react. It will be appreciated, however, that the resulting reaction product can be produced directly from a reaction between the added reagents or from an intermediate from one or more of the added reagents, which can be produced in the reaction mixture.

The term "biomass" as used herein includes materials containing cellulose, hemicellulose, lignin, protein and carbohydrates such as starch and sugar. Common forms of biomass include trees, shrubs and grasses, corn and cornhusks as well as municipal solid waste, waste paper and yard waste. Biomass high in starch, sugar, protein and oil, such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like. In some embodiments, the lignocellulosic biomass is selected from the group including, but not limited to, corn stover, straw, bagasse, miscanthus, sorghum residue, switch grass, bamboo, water hyacinth, hardwood, hardwood, softwood, wood chips, and wood pulp.

As used herein the term "pentosan" refers to a polysaccharide containing $C_5$ carbohydrates monomers.

As used herein, the term "carbohydrate" is defined as a compound that consists only of carbon, hydrogen, and oxygen atoms, wherein the ratio of carbon atoms to hydrogen to oxygen atoms is 1:2:1. Well-known examples of carbohydrates include sugars and sugar-derived oligomers and sugar-derived polymers.

The term "$C_5$ carbohydrate" refers to any carbohydrate, without limitation, that has five (5) carbon atoms in its monomeric unit. The definition includes pentose sugars of any description and stereoisomerism (e.g., D/L aldopentoses and D/L ketopentoses). $C_5$ carbohydrates can include (by way of example and not limitation) arabinose, lyxose, ribose, ribulose, xylose, and xylulose, in their monomeric, oligomeric and polymeric forms. Polymeric $C_5$ carbohydrates can contain several $C_5$ carbohydrate monomers and in some instances even contain some (lesser) amount of $C_6$ carbohydrate monomers.

The term "$C_6$ carbohydrate" refers to any carbohydrate, without limitation, that has six (6) carbon atoms in its monomeric unit. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose, in their monomeric, oligomeric and polymeric forms. Polymeric $C_6$ carbohydrates can contain several $C_6$ carbohydrate monomers, and in some instances even contain some (lesser) amount of $C_5$ carbohydrate monomers.

"Cellulose", as used herein, refers to a polysaccharide of glucose monomers $((C_6H_{10}O_5)_n)$; the term "cellulosic biomass" as used herein refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose and other $C_5$ carbohydrates, as does hemicellulose.

As used herein, the term "lignocellulosic" means, comprising cellulose, lignin and hemicellulose.

As used herein, the term "hemicellulosic" refers to a material comprising $C_5$ and $C_6$ sugar polymers. Hemicellulose consists of short, highly branched chains of sugars. It contains five-carbon sugars (usually D-xylose and L-arabinose) and six-carbon sugars (D-galactose, D-glucose, and D-mannose) and uronic acid, as well as some deoxy sugars in select instances. The sugars are partially acetylated. Typically the acetyl content is 10 to 15 wt %, based on the hemicellulose or 2 to 3 wt %, based on the biomass.

As used herein, the term "lignin" or "lignin feed" in the process of this invention refers to a polyphenols material comprised of phenolyl propane units linked by carbon-oxygen and carbon-carbon bonds. Lignins can be highly branched and can also be crosslinked. Lignins can have significant structural variation that depends, at least in part, on the plant source involved. Lignin is present as virgin lignin in unprocessed lignocellulosic materials. However, lignins can also include any type of lignin material that is extracted or produced from lignocellulose, independent of its source of method of production. Suitable lignin materials include, but are not limited to, Kraft lignins (a by-product of the paper industry), organosolve lignins, lignins derived as a byproduct of ethanol production processes, lignins derived from waste, including municipal waste, lignins derived from wood or wood products, as well as from agricultural products or waste, and various combinations thereof.

The term "elevated pressure," in the context of the processes of the present invention, refers to a pressure above atmospheric pressure (e.g., 1 atm at sea level) based on the elevation, for example at least 20, 30, 40, 50, 60, 70, 80, 90, 100, 110, 120, 130, 140, 150, 160, 170, 180, 190, 200, 225, 250, 275, 300, 325, 350, 375, or 400 psi (or greater), as well as pressures between any two of these values (e.g., 185 psi or 215 psi) at sea level.

The term "elevated temperature," as used herein, refers to a temperature above ambient temperature, for example at least about 100, 110, 120, 130, 140, 150, 160, 170, 180, 190, 200, 210, 220, 230, 240, or 250 degrees Celsius (° C.) or greater.

The term "dehydration", as used herein, refers to the removal of a water molecule from a molecule that contains at least one hydroxyl group.

The term "hydrolysis" as used herein refers to breaking the glycosidic bonds in polysaccharides to yield simple monomeric and/or oligomeric sugars. For example, hydrolysis of cellulose produces the six carbon ($C_6$) sugar glucose, whereas hydrolysis of hemicellulose produces the five carbon ($C_5$) sugars xylose and arabinose, together with other sugars. Hydrolysis can be accomplished by acid treatment or by enzymes such as cellulase, β-glucosidase, and xylanase.

The term "tar", as used herein, refers to the generic reference to organic material which is insoluble in water, which is dark in color, and which tends to become viscous and very dark to almost black when concentrated. Tar can be formed during heating of organic material, for example by pyrolysis, but is also formed when carbohydrates are subjected to acid hydrolysis, particularly when done at high temperatures. The presence of tar is undesired for a number of reasons. Tar may negatively affect the performance of the bio-based product in the application. For this reason, tar is preferably removed before further steps.

As used herein, the term "humins" refers to the dark, amorphous and undesirable acid byproducts and resinous material resulting from acid-induced sugar and other organic compound degradation. Humins may also be produced by acid hydrolysis of carbohydrates. Yang and Sen [Chem. Sus. Chem., Vol. 3, pp. 597-603 (2010)] report the formation of humins during production of fuels from carbohydrates such as fructose, and speculate that the humins are formed by acid-catalyzed dehydration. The molecular weight of humins can range from 2.5 to 300 kDa.

As used herein, the term "miscible" refers to a mixture of components that, when combined, form a single phase (i.e., the mixture is "monophasic") under specified conditions (e.g., component concentrations, temperature).

As used herein, the term "immiscible" refers to a mixture of components that, when combined, form a two, or more, phases under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two immiscible liquid phases, for example, an aqueous phase and a water-immiscible organic solvent phase. The term "biphasic" can also be used to describe a method employing such a reaction medium.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

DETAILED DESCRIPTION

The figures described above and the written description of specific structures and functions below are not presented to limit the scope of what Applicants have invented or the scope of the appended claims. Rather, the figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the figures and are not intended to limit the scope of the invention or the appended claims.

Applicants have created methods and processes for the production of valuable organic products and alcohols from pentosan-comprising biomass materials using an efficient process having numerous advantages over prior production methods. For example, process decreases the need for using fresh water during the process, due to the ability to recycle water from phase separations back into the process stream, thereby reducing the number and volume of waste water streams; thus, solvents and energy are used in an efficient manner. Further, the process allows for the controlled return of the slightly acidic aqueous stream following the dehydration of the $C_5$ product stream allows for maintaining an optimized reaction process flow. The recycle of the acid streams offers the advantage of limiting the input volume and associated costs of feeding fresh acid into the process, and the need and cost associated with using bases to neutralize the acid stream prior to disposal of the acid-containing waste water stream.

The process allows for the controlled return of organic solvent streams following the target product isolation and removal, thereby decreasing the volume of organic solvents necessary to the reaction process and increasing the efficiency of solvent usage throughout the process. Additionally, the method allows for increased amounts (an increased yield) of the furfural or other furan-type compounds to be formed as the end product of the reaction because as the $C_5$-carbohydrate containing intermediate (such as xylan) is formed, the furfural is thereafter immediately formed and removed, thereby decreasing the amount and frequency of byproducts found in multi-step processes. Furthermore, the process methods allow for higher concentrations of pentosan-comprising biomass materials to be treated, which increases the product concentration (e.g., increased production of furfural) overall. In addition, the use of extraction methods within the process allows for purification of the organic process stream without the inclusion of unwanted side-product impurities or humins, thus increasing the overall process production yield.

The chemistry of the general process of the one-step production route for the formation and production of furfural or other furan derivatives from biomass can be represented schematically as scheme (I), below:

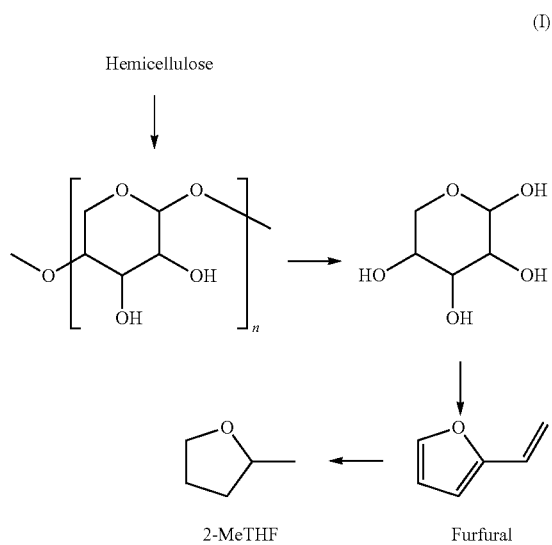

(I)

Figure 2:
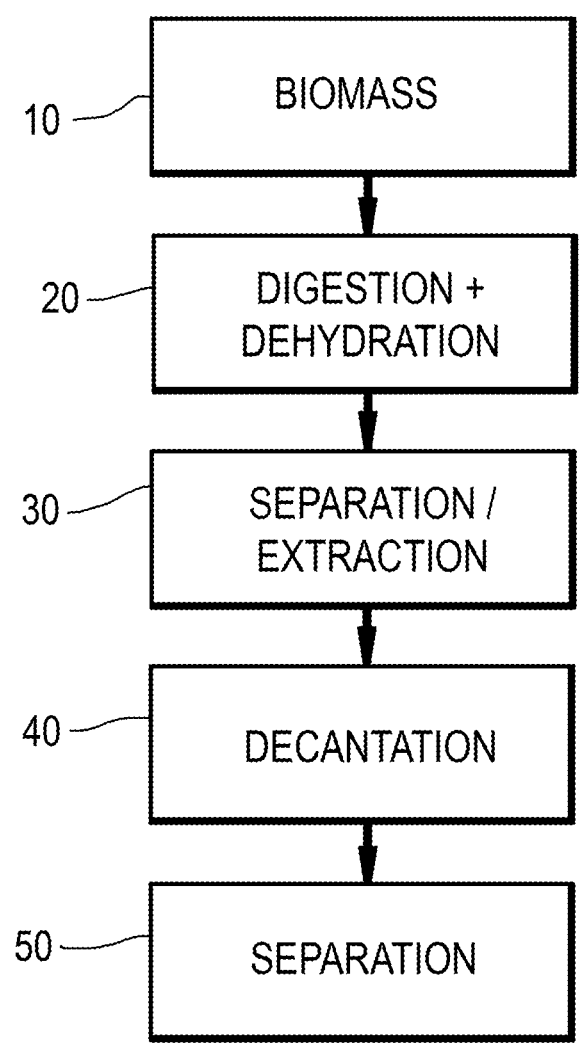
FIG. 2 illustrates a block flow diagram of the general steps of the closed-loop process of the present invention.
Figure 3:
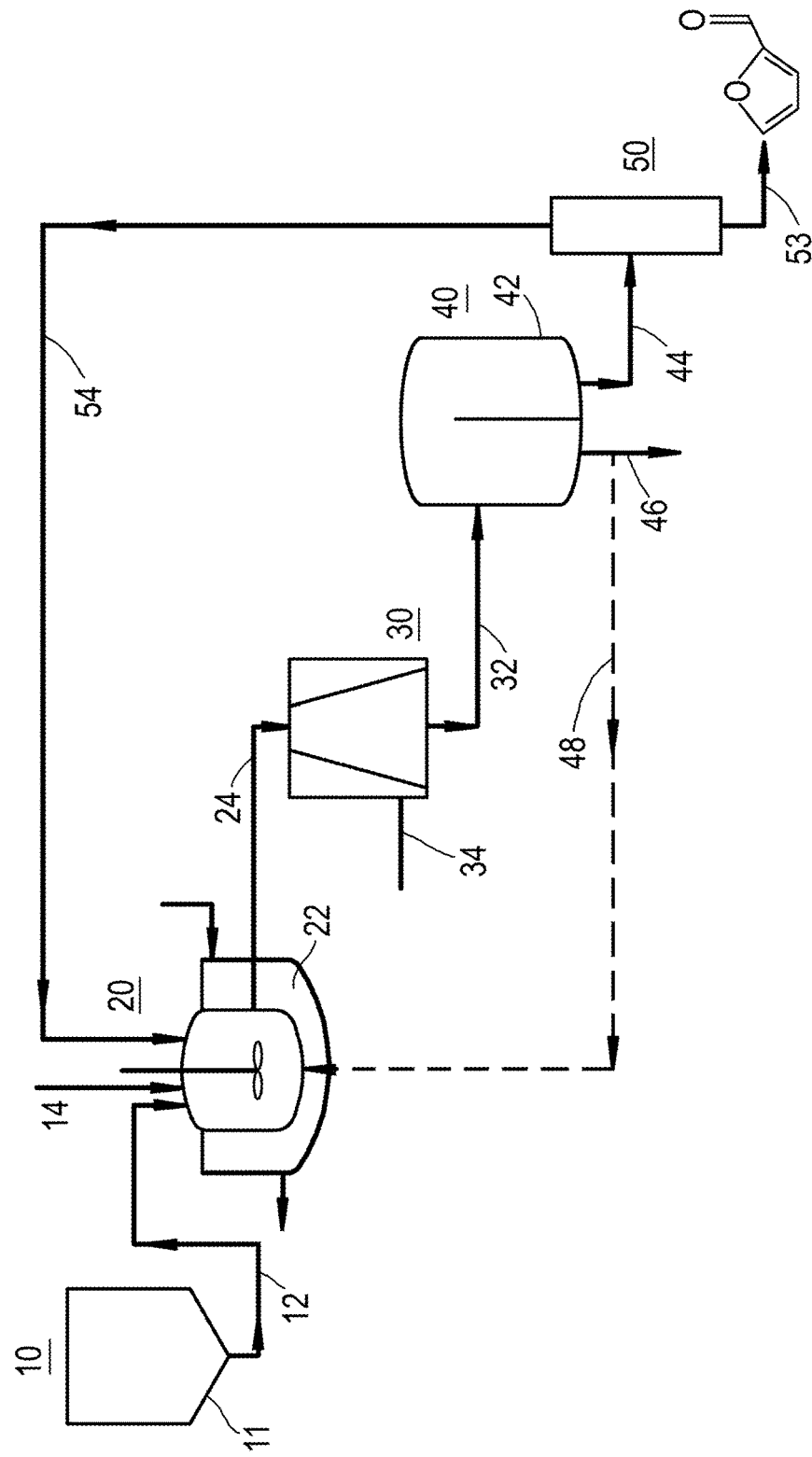
FIG. 3 illustrates a process flow diagram for an exemplary production process in accordance with select aspects of the present invention.

Turning now to the figures, FIG. 2 illustrates a general block flow diagram of an exemplary process in accordance with the present invention. FIG. 3 illustrates a detailed process flow diagram for the process of FIG. 2. These figures will be described in conjunction with each other. As illustrated in the process flow diagram of FIG. 2, the single-step process of the present disclosure includes providing a pentosan-comprising biomass, followed by a digestion and dehydration step 20, and thereafter the separation of solid and liquid product streams 30, the liquid furfural containing product stream proceeding to a decantation step 40 of the aqueous phase from the organic phase, the organic phase advancing to a separation step 50 wherein furfural or other furan derivatives are isolated, while the aqueous phase may be metered back into the digestion and dehydration step 20 so as to control the pH and the solids-to-liquids content within the digester and optimize the digestion process during a continuous loop production. The organic solvent removed during separation process 50 can also be fed back into the digester 22 for digestion and dehydration step 20 so as to reduce the amount of organic solvent to be added during the continued production process.

Biomass Processing

The biomass material 10 (shown in biomass container 10) can be used in a wet, dry or substantially dry form, and introduced directly into a digestion vessel 22 (also referred to herein as a digester), and may be pre-ground or not. For example, the pentosan-comprising biomass material used can sized by grinding to a desired particle size prior to introduction to the digester 22. In a non-limiting example, the biomass can be ground to a particle size in the range of about 0.1 mm to about 10.0 mm, about 0.1 mm to about 5.0 mm, or about 0.1 mm to about 2.0 mm. In the instance that the biomass is ground and/or sized to a specific particle size, the particle size can be selected such that the digestion process occurs with the highest efficiency. Digestion vessel 22 can be jacketed, such as with a water-cooling jacket (as shown), or not, as appropriate.

The pentosan-comprising biomass material 10, whether ground or not, can also be mixed with water to form a slurry of a desired consistency prior to introducing the biomass to the digester 22, and to facilitate hydrolysis. For example, the slurry can be in the range of from about 5 wt % solids to about 100 wt % solids by weight, e.g., about 10 wt %, about 20 wt %, about 30 wt %, about 40 wt %, about 50 wt %, about 60 wt %, about 70 wt %, about 80 wt %, about 90 wt %, or about 100 wt % solids by weight, as well as slurry concentrations within these ranges, e.g., about 25 wt % by weight, or about 5 wt % by weight.

In accordance with select aspects of the present invention, the pentosan-comprising biomass material 10 that is advanced to the digester 22 may further include or be mixed with an aqueous liquid (water) or liquids from other, downstream steps in the process, such as fluid stream 48 which may optionally contain acids or bases from the process, or by an addition step prior to reintroduction into the digester. The pentosan-comprising biomass material 10 may optionally also be separated into a liquid phase and a solids phase using any suitable separation method, including centrifugation, decanting, filtration and flocculation, so as to dilute or adjust the biomass in the initial steps of the process to optimize production.

The pentosan-comprising biomass material 10 suitable for use herein includes materials containing cellulose, hemicellulose, lignin, protein and carbohydrates such as starch and sugar. Common forms of biomass include trees, shrubs and grasses, corn and cornhusks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste.

In accordance with a non-limiting aspect of the invention, the biomass is a lignocellulosic material such as bagasse comprising from about 30 wt % to about 50 wt % cellulose, from about 15 wt % to about 40 wt % hemicellulose (including xylose), from about 10 wt % to about 25 wt % total lignin (including both acid insoluble and acid soluble lignins), and an ash content ranging from about 1 wt % to about 10 wt %.

Digestion and Dehydration

As shown in FIG. 3, in the next step of the production process, the pentosan-comprising biomass material 10 is introduced from container 11 into a digester 22, using any suitable introducing methods, such as via a screw extruder or by way of a material addition pipe stream.

In the digestion step 20, the biomass is admixed with water, and at least one water-immiscible organic solvent, such as methyl-THF, toluene, sec-butyl phenol (SBP) or the like, to a target solid-to-liquid (S:L) concentration, or if already in slurry form, adjusted to the appropriate concentration ratio. The biomass may have already contained water, either inherently or provided as part of a biomass pretreatment. The solid to liquid (i.e. water and water-immiscible organic solvent) weight ratio within the digester 22 preferably ranges from about 1:3 to 1:30, preferably about 1:3 to about 1:15, more preferably from about 1:6 to about 1:15, still more preferably from about 1:6 to about 1:10, even still more preferably from about 1:8 to about 1:10.

The water to water-immiscible organic solvent weight ratio within the digester 22 preferably ranges from about 10:1 to 1:5, preferably about 9:1 to about 1:3, more preferably from about 3:1 to about 1:2.

The digestion process step is carried out at an elevated temperature, preferably above about 100° C., including in the range from about 100° C. to about 250° C., and from about 110° C. to about 200° C., and from about 140° C. to 180° C., for a period of time ranging from about 1 minute to about 24 hrs, preferably from about 5 minutes to about 12 hrs, more preferably from about 10 minutes to about 6 hrs., even more preferably 30 minutes to 4 hrs., still more preferably 30 minutes to 2 hrs.

The digestion step also includes the optional addition of one or more acids, or buffer solutions, to the digester 22 via acid stream 14, so as to adjust the pH of the digestion reaction and maintain it with a selected pH range. Preferably, the pH is less than about pH 5, more preferably less than about pH 3, and most preferably less than about pH 1. Preferably, a pH range is used in the range of from 0 to 5, more preferably of from 0 to 4, even more preferably of from 0 to 3, still more preferably of from 0 to 2. Any suitable digester equipment known in the art may be used.

In accordance with preferred aspects of the invention, the acid catalyst introduced into the digester is introduced by an acid stream 14, by way of an aqueous process loop recycle stream 48, or both, and is introduced in amounts and at a rate so as to optimize the digestion process. The acid catalyst is preferably an inorganic acid, most preferably a mineral acid such as HCl, $HNO_3$, $H_2SO_4$, $H_3PO_4$, $H_3BO_3$, and the like. Organic acids, e.g., acetic acid, formic acid, oxalic acid, levulinic acid, citric acid, etc.), zeolites (Si/Al from 1 to 100), acid and super-acid resins (e.g., cation exchange resin), phosphates ($NbOPO_4$, vanadium phosphate) solid silica-, silica-alumina, and titania-based supports functionalized by acid groups, and other Lewis acids may also be used.

In one particular example, some types of biomass that may be used as the starting material intrinsically contain acids or will form acids upon being subjected to the digestion, examples of such acids intrinsically contained or formed include, but are not limited to, formic acid or acetic acid. When using such types of biomass, the need to add acid may be reduced or even eliminated as the in-situ generated acid will provide the necessary acidic pH.

The amount of acid to be added, or the amount present within the digestion slurry, is preferably adjusted to be in the range from about 0.1 wt % to about 10 wt % acid.

Alternatively, a basic, preferably caustic pretreatment could be used instead of the acid pretreatment, this would however require a subsequent treatment to lower the pH of the aqueous C5 sugar feed stream prior to the conversion of the C5 sugar.

During the digestion process step, at least part, and preferably substantially all, of the pentosan in the biomass material is released from the biomass in the form of $C_5$-carbohydrate compounds. In the presence of the acid at least part of, and preferably substantially all of the $C_5$-carbohydrate compounds are subsequently converted to furfural. Optionally, other furan derivatives may also be formed. Due to the nature of the furfural, and optional other furan derivatives, the furfural preferably resides in the organic solvent.

The preferred organic solvent for use in the present invention comprises a water-immiscible organic solvent that is immiscible with the aqueous phase containing insoluble cellulose and lignin byproducts. Preferably such water-immiscible organic solvents have a maximum water solubility of less than about 30 wt %, preferably less than about 10 wt %, and most preferably less than about 2 wt % at ambient (room) temperature. The preferred organic solvents are 1-butanol, sec-butyl phenol (SBP), MIBK, toluene, and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), cyclic alcohols (e.g., cyclohexanol), straight or branched alkanones (e.g. butanone (i.e., methylethyl ketone (MEK)), pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Aliphatic and cycloaliphatic ethers (e.g., dichloroethylether, dimethyl ether, MTHF), saturated and unsaturated aliphatic or aromatic hydrocarbons (decane, toluene, benzene, cymene, 1-methyl naphthalene), oxygenated hydrocarbons (e.g. furan, nonyl phenol, etc.), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like). Lignin derived solvents such as Guaiacol, Eugenol, 2-Methoxy-4-propylphenol (MPP), 2-Methoxy-4MethylPhenol (MMP) or mixture thereof may also be used. Combination of solvents can also be used to fine tune the extracting capability of the solvent.

Preferably, the organic solvent or the combination of organic solvents can extract 80 mol % or more of the furfural produced from the aqueous phase, while at the same time dissolve less than 1 wt %, more preferably less than 0.1 wt %, more preferably less than 0.01 wt % of water, based on the organic solvent.

The organic phase may also be an oxygenated hydrocarbon that is generated as an end-product from the process of the invention.

Due to the preference of the formed furfural to reside in the organic phase in rather than in the aqueous phase at least part of the formed furfural, and preferably more than 50 mol %, still more preferably more than 75 mol %, even still more preferably more than 80 mol % of the formed furfural will dissolve in the organic phase.

Separation

With continued reference to FIG. 3, once the digestion process is complete, the digestion process stream 24 is transferred to a solid-liquid extractor 30 or phase separator, where the solids product stream 34 comprising primarily insoluble cellulose and lignin is separated from the liquid product stream 32 that contains primarily furfural, water, and the organic solvent, whereby the furfural is predominantly dissolved in the organic solvent. The liquid product stream 32 is then fed into a liquid-liquid decantation/separation vessel 42 for separating the liquid product stream into an aqueous stream 46 and an organic product stream 44.

Product Recovery

Although, part of organic product stream 44 may be recycled to directly to the digestion step, the majority of organic product stream 44 is subjected to a separation step, preferably one or more distillation steps, in separation zone 50. Organic product stream 44, containing the target organic compounds such as furfural, or optionally other furan derivatives or furfural precursors, such as HMF, methyl-furfural and oligomeric furanic species). Residual water from the reaction that was not removed during the liquid-liquid extraction step, and which may contain acetic acid or other water-soluble impurities, may be removed in separation zone 50, with recovery of furfural via stream 53.

Following the removal of the furfural and optional other product and impurities, the organic solvent is retrieved as organic solvent stream 54 from separation zone 50. At least part of the organic solvent may be recycled back into the process, preferably by recycling the organic solvent back to the digestion vessel 22, in order to minimize production costs and maintain the reaction process and reaction efficiency. Alternatively, the organic solvent stream 54 can directed to a further solvent purification process (not shown) such as column distillation/separation or solvent-solvent extraction, prior to reintroduction back into the production process, so as to remove impurities, primarily humins (heavy byproducts), as well as purify the solvent before the reintroduction step. Fresh solvent may be added to the organic solvent stream 54 prior to reintroduction to the digestion reaction vessel 22, to make up for any organic solvent losses.

The aqueous stream 46, following liquid-liquid separation/decantation step 40, may undergo a neutralization, wherein bases are added to the aqueous phase stream to bring the pH of the stream 46 to approximately neutral, e.g., pH 6.8-7.1, after which the aqueous stream may be further processed as waste water. Preferably at least part of the aqueous phase stream 46 redirected to the digester 22 via flow stream 48, with the optional addition of acid as necessary to adjust the pH of flow stream 48 to the required acidity level prior to reintroduction into the digester 22.

The solids product stream 34 will, in addition to solids, still comprise a significant amount of organic solvent. Recovering this organic solvent has the advantage that less organic solvent is lost from the process and, consequently, less make-up organic solvent needs to be provided to the process to replenish the organic solvent lost via the solids removal. In addition to the reduction of the organic solvent loses, recovering the organic solvent from the solids product stream will also allow for the recovery of additional furfural that is dissolved in the organic solvent. As such the furfural yield may be further increased. Therefore, process according to the invention further comprises a step (f) providing treating the solids product stream to further remove, residual, organic solvent to yield an organic solvent-depleted solids product stream and organic solvent. The organic solvent can be recovered from solid residues separated as stream 34 during this single-step process in a number of ways, including but not limited to:

(1) washing the solids with an aqueous fluid stream, preferably effluent stream 48 obtained after step 40. Optionally, the solids may be washed with effluent stream 48 two or more times or additional fresh water may be added to steam 48 to ensure the solids are washed with a sufficient volume to remove a significant amount of the residual solvent. Following contact with the solids effluent stream 48 is preferably treated to remove salt prior to recycling stream 48 to the digestion step;

(2) atmospheric or vacuum evaporation of the organic solvent, optionally together with any residual water;

(3) washing the solid residue with (a) a light (molecular weight) wash solvent, either water miscible or immiscible, or (b) a near-critical or super-critical solvent, preferably supercritical $CO_2$, supercritical C2 to C4 hydrocarbons or mixture of hydrocarbons like e.g. super critical LPG. The solids may optionally subsequently be dried to recover the wash solvent, followed by distillation of the wash solvent to purify the wash solvent from humins and extraction solvent.

Alternatively, the solids in solids product stream 34 may first be treated, preferably washed, with an organic solvent to remove the residual organic solvent and subsequently be treated, preferably washed, by an aqueous stream to remove any residual salts that were deposited on the solids. The removal of these residual salts has the benefit that the solids will be more suitable for further processing, as explained herein below, wherein the presence of salt is seen as a disadvantage. Preferably, effluent stream 48 obtained after step 40 is used as the aqueous stream. Optionally, the solids may be treated with effluent stream 48 two or more times or additional fresh water may be added to steam 48 to ensure the solids are washed with a sufficient volume to remove a significant amount of the residual solvent. Following contact with the solids effluent stream 48 is preferably treated to remove salt prior to recycling stream 48 to the digestion step (b).

Any recovered organic solvent may be recycled back to the digestion step (b).

The solids removed during various steps of the process described herein, but in particular in the solids product stream or organic solvent-depleted solids product stream, can be converted to power or energy, such as by burning or otherwise treating the solids in a power plant or similar power production facility, the power being storable for later sale, or used to fuel the process described herein, thereby increasing the process efficiency. The solid char and/or humins can also be converted to a fuel gas, such as by gasification methods to produce low tar fuel gas with low emissions and no toxic waste streams.

The following examples are included to demonstrate preferred embodiments of the inventions. It should be appreciated by those of skill in the art that the techniques disclosed in the examples, which follow represent techniques discovered by the inventors to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the scope of the inventions.

EXAMPLES

General Methods and Materials
Digestion and Biphasic Dehydration in a Single Step Digestion and biphasic dehydration was carried out in a 500 ml zipperclave reactor (Autoclave Engineers, Inc.). Biomass (eg. Bagasse) is weighed and placed in the reactor. The composition of the biomass (bagasse) charged is given in Table 1. In a typical run aqueous stream containing 1% $H_2SO_4$ acid was charged along with equal amount of immiscible organic solvent at a certain solid:water:organic solvent (S:W:L) ratio. The reactor is then heated to the reaction temperature and held at that temperature for the residence time indicated in the examples below. After the reaction is complete the solids is separated from the slurry reactor mixture by filtration using house vacuum system. After filtration, the filtrate was weighed and transferred into a separatory funnel to allow for two liquid phases to separate. After liquid-liquid separation each phase was weighed and analyzed for its content. The aqueous phase was analyzed using high-performance liquid chromatography (HPLC) and the organic phase was analyzed using gas chromatography (GC). The wet solid cake on the filter is further washed with equal amount of water to recover any free solvent trapped in the solids. The residual biomass is then dried and used for solids analysis. Compositional analysis of the residual biomass is carried out to determine the carbohydrate and lignin content.

Analytical Methods

Solids compositional analysis of the feedstock the digested biomass samples were conducted using standard TAPPI (T-222, T-211, T-249) methods.

The aqueous phases from digestion/dehydration runs were analyzed and quantified for various components such as glucose, xylose, arabinose, mannose, formic acid, acetic acid, levulinic acid, furfural using high-performance liquid chromatography (HPLC) system (Shimadzu) equipped with a refractive index detector (Shimadzu) on a BIO-RAD 87H Column. Prior to injection, the samples were filtered through 0.45 μm HV filters (Millipore, Bedford, Mass., USA), and a volume of 10 μL was injected. The mobile phase for the column was 5 mM H2SO4 in Milli-Q water at a flow rate of 0.6 mL/min.

The furfural concentration in the organic phase was measured using GC. Agilent 6890 GC with a DB-1301 capillary column installed in its split/splitless inlet was used with the FID. The column parameters were 30 m length, 0.25 mm ID, and 1.0 μm film thickness. Method parameters were as follows:

Oven Temp Program: 40° C. Hold 3 min, Ramp 10° C./min to 280° C., Hold 3 min, Inlet Temp 250° C., Injection Volume 1.0 μl, Split ratio 100:1, Constant Pressure 20 psi Helium Carrier gas,
Detector Temp 325° C., H2 flow 35 ml/min, Air 400 ml/min, and Helium Makeup 25 ml/min.

Calculations

Solids dissolved was calculated as weight percentage ratio of oven dried digested biomass material to the total amount of feed (on dry basis).

Xylan recovery as xylose accounts for how much xylan is removed as xylose during digestion/dehydration.

Xylan Recovery as Xylose=132/150*[wt. of Xylose]$_{AP}$/[wt. of Xylan]$_{feed}$

Xylan Recovery as Furfural indicates how much of xylan is in the form of furfural at digestion/dehydration conditions.

Xylan Recovery as Furfural=132/96*{[wt. of Furfural]$_{AP}$+[wt. of Furfural]$_{OP}$}/[wt. of Xylan]$_{feed}$ Total Recovery of Xylan=Xylan Recovery as Xylose+Xylan Recovery as Furfural The subscript "OP" refers to organic phase.
The subscript "AP" refers to aqueous phase.

Biomass Composition

In table 1, the composition of the biomass used in the examples is shown. For hemicellulose and lignin a further division into the separate components is also provided in table 1.

TABLE 1

Biomass (Bagasse) composition used
Bagasse composition (wt % on dry basis)

| | | |
|---|---|---|
| Cellulose | 40 | |
| Hemicellulose | 28.5 | |
| Glucoronic Acid | | 0.7 |
| Xylose | | 22.8 |
| Arabinose | | 2.2 |
| Acetic Acid | | 3.9 |
| Total Ligin | 18 | |
| Acid Insoluble Lignin | | 16.75 |
| Acid Soluble Lignin | | 1.25 |
| Total Ash | 3.5 | |
| Extractives (Ethanol) | 9.75 | |
| Total | 99.75 | |

Example 1: Single Step Conversion of Biomass to Furfural

For each run, fresh biomass was charged into a batch reaction vessel described above at a selected biomass:water: organic solvent (S:W:L) ratio and stirred. The reactions were performed for a certain period of time, at 1% H2SO4 acid concentration and temperature as indicated in is Table 2. Sec-butylphenol (SBP) and Toluene were used as extracting organic solvent. The reaction mixture was then filtered, the filtrate was collected and transferred to a separatory funnel for liquid-liquid separation. The aqueous phase was analyzed via HPLC for xylan recovery and the organic phase using GC for furfural concentration. The solid remaining on the filter was further washed with equal amount of water to recover any free solvent trapped in the solids. The wet solids were then dried in a drying oven equipped with a vacuum trap (to collect solvent and/or water), and analyzed for its content.

TABLE 2

Single step conversion of biomass xylan to furfural. All runs were conducted with 1% $H_2SO_4$ acid concentration in water.

| Run | Solvent | S:W:L weight ratio | T [° C.] | time [min] | Solids dissolved [wt %] | Xylan recovery as xylose [wt %] | Xylan recovery as furfural [wt %] | Total xylan recovery [wt %] |
|---|---|---|---|---|---|---|---|---|
| 1 | SBP | 1:4:4 | 170 | 30 | 45% | 29% | 13% | 42% |
| 2 | SBP | 1:4:4 | 170 | 45 | 60% | 26% | 34% | 60% |
| 3 | SBP | 1:4:4 | 160 | 30 | 50% | 42% | 8% | 50% |
| 4 | SBP | 1:4:4 | 160 | 60 | 43% | 37% | 37% | 74% |

TABLE 2-continued

Single step conversion of biomass xylan to furfural. All runs were conducted with 1% H₂SO₄ acid concentration in water.

| Run | Solvent | S:W:L weight ratio | T [° C.] | time [min] | Solids dissolved [wt %] | Xylan recovery as xylose [wt %] | Xylan recovery as furfural [wt %] | Total xylan recovery [wt %] |
|---|---|---|---|---|---|---|---|---|
| 5 | SBP | 1:8:8 | 170 | 60 | 67% | 14% | 60% | 75% |
| 6 | SBP | 1:8:8 | 160 | 60 | 65% | 31% | 43% | 74% |
| 7 | SBP | 1:6:6 | 160 | 60 | 59% | 33% | 43% | 76% |
| 8 | Toluene | 1:8:8 | 160 | 60 | 47% | 32% | 43% | 74% |
| 9 | Toluene | 1:6:6 | 160 | 60 | 51% | 36% | 41% | 76% |

Results demonstrate use of an organic solvent in the presence of biomass to hydrolyze xylan to make xylose and subsequent conversion of xylose to furfural in the aqueous phase with simultaneously extracting furfural from the aqueous phase into the organic solvent. In all cases, almost 99% of xylan was removed from the biomass as indicated by solids analysis. As seen about 40-60% yields of furfural can be obtained depending on the process conditions of the experiments. By combining digestion (i.e. extracting xylan from biomass) and biphasic acid dehydration (furfural formation step) overall capex of the reactor system and hence the process can be minimized.

Other and further embodiments utilizing one or more aspects of the inventions described above can be devised without departing from the spirit of Applicant's invention. For example, select steps within a loop system can be done a multiple number of times in order to optimize throughput of the system and product recovery. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

That which is claimed is:

1. A process for converting biomass into furfural, the process comprising the steps of:
   (a) providing a pentosan-containing biomass material;
   (b) subjecting the pentosan-containing biomass material to an acid catalyzed digestion process and a dehydration reaction in a digestion vessel at a temperature greater than about 100° C. in the presence of an acid, water and a water-immiscible organic solvent to produce a digested product stream comprising water, organic solvent, furfural and solids;
   (c) separating the digested product stream into a liquid product stream and a solids product stream, the liquid product stream comprising water, organic solvent and furfural;
   (d) subjecting the liquid product stream to a liquid-liquid extraction for a period of time sufficient to separate the liquid product stream into an aqueous stream and an organic product stream, the organic product stream comprising furfural;
   (e) separating furfural from the organic product stream to yield furfural and organic solvent; and
   (f) treating the solids product stream to further remove organic solvent to yield an organic solvent depleted solids product stream and recovered water-immiscible organic solvent.

2. The process of claim 1, wherein at least part of the organic solvent yielded in step (e) and/or step (f) is recycled to step (b).

3. The process of claim 1, wherein the mixture comprising pentosan containing biomass material, water and a water-immiscible organic solvent has a solid-to-liquid weight ratio ranging from about 1:3 to about 1:30.

4. The process of claim 3, wherein the mixture comprising pentosan containing biomass material, water and a water-immiscible organic solvent has a solid-to-liquid weight ratio ranging from about 1:6 to about 1:10.

5. The process of claim 1, wherein the mixture comprising pentosan containing biomass material, water and a water-immiscible organic solvent has a water-to-water-immiscible organic solvent weight ratio ranging from about 9:1 to about 1:3.

6. The process of claim 1, wherein the acid catalyst in the digestion process, the dehydration process, or both is selected from the group consisting of inorganic acids.

7. The process of claim 1, wherein the acid catalyst in the digestion process, the dehydration process, or both, is a mineral acid selected from the group consisting of HCl, HNO₃, H₂SO₄, H₃PO₄, and H₃BO₃.

8. The process of claim 1, wherein the liquid product stream separated from the solids product stream following digestion comprises furfural in a concentration ranging from about 0.1 wt % to about 15 wt %.

9. The process of claim 1, wherein the liquid product stream comprises furfural a concentration ranging from about 0.2 wt % to about 10 wt %.

10. The process of claim 1, wherein at least part of the aqueous stream of step (d) is recycled to step (b).

11. The process of claim 1, wherein the temperature in step (a) is in the range of from about 100° C. to about 250° C.

12. The process of claim 1, wherein the pH in step (a) is less than pH 5.

13. The process of claim 1, wherein part of the organic product stream comprising furfural from step (d) is directly recycled to step (b).

14. The process of claim 1, wherein solids in the solids product stream are converted into alcohol, glycol, acid, power, energy, or a fuel gas.

15. The process of claim 1, wherein the treating the solids product stream comprises washing the solids, evaporation of the solvent, or a combination thereof.

* * * * *